(12) United States Patent
Biber

(10) Patent No.: US 9,697,936 B2
(45) Date of Patent: Jul. 4, 2017

(54) MATERIAL FOR USE IN A MAGNETIC RESONANCE INSTALLATION, METHOD FOR MANUFACTURING SAID MATERIAL, AND MAGNETIC RESONANCE INSTALLATION

(71) Applicant: Stephan Biber, Erlangen (DE)

(72) Inventor: Stephan Biber, Erlangen (DE)

(73) Assignee: SIEMENS AKTIENGESELLSCHAFT, München (DE)

( * ) Notice: Subject to any disclaimer, the term of this patent is extended or adjusted under 35 U.S.C. 154(b) by 1074 days.

(21) Appl. No.: 13/847,595

(22) Filed: Mar. 20, 2013

(65) Prior Publication Data
US 2013/0249556 A1    Sep. 26, 2013

(30) Foreign Application Priority Data
Mar. 22, 2012 (DE) .................. 10 2012 204 567

(51) Int. Cl.
| | | |
|---|---|---|
| *H01F 1/01* | (2006.01) | |
| *G01R 33/34* | (2006.01) | |
| *G01R 33/565* | (2006.01) | |
| *H01F 1/00* | (2006.01) | |
| *A61B 5/055* | (2006.01) | |

(52) U.S. Cl.
CPC .............. *H01F 1/01* (2013.01); *G01R 33/34* (2013.01); *G01R 33/565* (2013.01); *G01R 33/56536* (2013.01); *H01F 1/0018* (2013.01); *A61B 5/0555* (2013.01); *G01R 33/34007* (2013.01)

(58) Field of Classification Search
CPC ....... H01F 1/01; H01F 1/0018; G01R 33/565; G01R 33/56536; G01R 33/34; G01R 33/34007; A61B 5/0555
See application file for complete search history.

(56) References Cited

U.S. PATENT DOCUMENTS 4,310,565 A * 1/1982 Lehner ................ G11B 5/7021
427/128
5,987,672 A    11/1999 Oosterwaal
(Continued)

FOREIGN PATENT DOCUMENTS

| DE | 19711610 A1 | 10/1997 |
|---|---|---|
| DE | 102004015859 A1 | 10/2005 |

(Continued)

OTHER PUBLICATIONS

Schenck, J. F.: The role of magnetic susceptibility in magnetic resonance imaging: MRI magnetic copatibility of the first and second kinds. In: Med. Phys. 23 (6), 1996, pp. 815-850; 1996.

(Continued)

*Primary Examiner* — G. M. Hyder

(57) ABSTRACT

A material for a magnetic resonance installation is provided, wherein the material includes a support material and a magnetic doping material which is admixed in a specific proportion. The doping material exhibits an anisotropic susceptibility. In respect of the anisotropic susceptibility, the doping material exhibits a mean orientation along a predefined direction. An essentially homogeneous intermixture of the support material and the doping material is present within a volume of the material which is smaller than 1 mm$^3$.

18 Claims, 4 Drawing Sheets

(56) References Cited

U.S. PATENT DOCUMENTS

| | | | |
|---|---|---|---|
| 7,604,875 B2 | 10/2009 | Wagner | |
| 2012/0249142 A1* | 10/2012 | Biber | G01R 33/387 |
| | | | 324/309 |

FOREIGN PATENT DOCUMENTS

| | | |
|---|---|---|
| DE | 102006025940 A1 | 12/2007 |
| DE | 102011006569 A1 | 10/2012 |

OTHER PUBLICATIONS

Garc C. Lee, et.al: "Pyrolytic Graphite Foam: A Passive Magnetic Susceptibility Matching Material" in Journal of Magnetic Resonance Imaging, 2010, vol. 32, pp. 684-691; 2010.

N. Knutson et.al.: Use of Colloidal Graphite Coating to Reduce Magnetic Resonance Imaging Artifacts Caused by Metallic Objects, Journal of Medical Devices, Jun. 2009, vol. 3, No. 2, 1 Page (Abstract) http://scitation.aip.org/getabs/servlet/GetabsServlet?prog=normal&id=JMDOA400000300000202754500002&idtype=cvips&gifs=yes&ref=no; 2009.

Praxis Dr. B. Sander: MR-Grundlagen www.mrx.de/mrpraxis/mrgrund.html;2011; Dec. 2, 2011.

* cited by examiner

MATERIAL FOR USE IN A MAGNETIC RESONANCE INSTALLATION, METHOD FOR MANUFACTURING SAID MATERIAL, AND MAGNETIC RESONANCE INSTALLATION

CROSS REFERENCE TO RELATED APPLICATIONS

This application claims priority of German Patent Application No. 10 2012 204 567.8 DE filed Mar. 22, 2012. All of the applications are incorporated by reference herein in their entirety.

FIELD OF INVENTION

The invention relates to a material for use in a magnetic resonance installation, a method for manufacturing said material, and a magnetic resonance installation comprising components that are made from said material. In particular, the invention relates to a material which exhibits reduced visibility in the context of magnetic resonance imaging.

BACKGROUND OF INVENTION

Magnetic resonance (MR) imaging is an imaging method used in many fields of medicine for the purpose of examination and diagnosis. It is based on the physical effect of nuclear spin resonance. For the purpose of recording MR signals, a basic magnetic field is established within an examination region by means of a basic field magnet, thereby aligning the magnetic moments of nuclei such as hydrogen nuclei H-1 or nitrogen nuclei N-14, for example.

The nuclear spins can be deflected or excited out of the aligned position parallel with the basic magnetic field, i.e. the position of rest, or out of another state, by means of irradiation using high-frequency (HF) pulses. During the relaxation into the position of rest, a decay signal is generated which can be inductively detected as an MR signal by one or more HF receive coils. For example, selective dephasing and rephasing of the nuclear spins by means of switching gradient fields in a suitable manner can generate an MR signal. Such an effect is used in so-called gradient echo MR recording sequences.

As a result of establishing a layer selection gradient when the high-frequency pulses are irradiated, nuclear spins are only excited in an examination object layer in which the resonance condition is satisfied due to the local magnetic field strength. Further spatial encoding can be achieved by establishing at least one phase coding gradient and one frequency coding gradient during the readout. It is thereby possible to obtain MR signals in a spatially resolved manner from a plurality of layers of a person being examined. Using suitable representation methods, a three-dimensional (3D) mapping of a specific region of the person being examined can be provided in this way for the purpose of diagnosis. A typical spatial resolution of the MR imaging in this context can be 1 mm in all three spatial directions, for example. Such a spatially distributed imaging point is referred to as a voxel.

For the purpose of MR imaging, a patient is generally moved into the interior of the basic field magnet on a couch or a table. In order to improve the MR imaging, use is also made of HF local coils which are placed in the immediate vicinity of the patient. The imaging space therefore contains not only the patient, but also other parts such as the couch and the coils, these being made from the widest variety of materials. However, these materials can likewise produce an image as they contain nuclei that are also used for the MR imaging.

Imaging properties of materials that are situated inside the examination region which is used for MR imaging can give rise to artifacts in the MR images. Such artifacts can result in incorrect diagnosis or render the image diagnostically unusable. Relatively few materials are known which exhibit reduced visibility in MR imaging in empirical tests. The number of usable materials is limited because, in addition to reduced visibility in the MR imaging, usability within an MR installation is also governed by other criteria such as little or no electrical conductivity and little or no magnetic susceptibility, for example.

Since it is not possible to utilize significantly less expensive plastic materials, for example, this can result in higher costs in the manufacture of components for use in the MR installation. Furthermore, e.g. such soft and flexible plastic materials as are found in various fields of everyday life cannot be used because as a solid material they do not exhibit reduced visibility in the MR imaging. This can result in reduced comfort and limited design freedom in the utilization and/or manufacture of components for use in an MR installation. Furthermore, it may not be possible to utilize materials that have particularly good working properties or are particularly robust or stable. This can result in reduced reliability or a reduced service life of the components to be used in the MR installation.

For example, U.S. Pat. No. 7,604,875 B2 discloses techniques which allow the magnetic susceptibility of support materials to be matched to fixed predefined values by means of adding paramagnetic and/or diamagnetic substances. However, the techniques disclosed therein relate to the mitigation of a susceptibility mismatch, as a result of which the static magnetic field varies on a length scale of several centimeters and deviates from the desired value of the basic magnetic field. This can result in the occurrence of displacements or spatial distortions in MR images, for example, or adversely affect the quality of spectral fat saturation techniques. However, the visibility of the materials in the MR imaging is not affected.

SUMMARY OF INVENTION

A requirement therefore exists for techniques which allow the provision of materials for use in components of an MR installation, said materials being free of the above cited disadvantages and having reduced MR visibility. In particular, a requirement exists for techniques which allow the provision of the widest possible variety of support materials having reduced MR visibility.

This object is achieved by the features in the independent claims. The dependent claims define embodiment variants.

According to one aspect, the invention relates to a material for use in a magnetic resonance installation, said material comprising a support material and a magnetic doping material that is admixed in a specific proportion. The doping material exhibits an anisotropic susceptibility. In respect of its anisotropic susceptibility, the doping material exhibits a mean orientation along a predefined direction. An essentially homogeneous intermixture of the support material and the doping material is present within a volume of the material which is smaller than 1 mm$^3$.

The magnetic doping material can be diamagnetic, paramagnetic or ferromagnetic, for example. The doping material can exhibit a magnetic susceptibility which differs from the magnetic susceptibility of the support material. For example, the support material can actually be non-magnetic, i.e. exhibit very little or no magnetic susceptibility. However, it is also possible for the support material to be magnetic.

An essentially homogeneous intermixture can mean, for example, that the specified proportion of the doping material is always present within arbitrarily disposed corresponding (test) volumes having a size that is less than 1 mm³. The admixture of the doping material can lead to inhomogeneities and local or microscopic variations in the concentration. This applies because local regions or clusters may exist where the doping material is present in a higher than average concentration or where the support material is present in a higher than average concentration. However, the admixture can be so fine or uniform that such inhomogeneities are not present in an observation that is averaged over the volume. In other words, a concentration gradient of the doping material may have values other than zero on a microscopic length scale or on a length scale smaller than 1 mm, while a concentration gradient that is specified or averaged over lengths of 1 mm or more can have values equal or close to zero.

As a consequence of admixing the magnetic doping material having a magnetic susceptibility $\chi \neq 0$, the magnetic field within the material varies locally from the basic magnetic field strength when the material is introduced into the basic magnetic field of the MR installation. This occurs e.g. due to the demagnetization effect of the magnetic doping material, which strengthens or weakens an external magnetic field. The corresponding physical phenomena of the static magnetic fields are known to a person skilled in that art and therefore require no further discussion in this context.

Microscopic inhomogeneities of the magnetic field are therefore generated as a result of the locally varying susceptibility. In particular, the magnetic field varies on a characteristic length that is proportionate to the fineness of the intermixing and the (microscopic) geometry of the doping materials, e.g. by a characteristic length of less than 1 mm, this being derived from the size of the volume. Such a homogeneous intermixture on a length scale of less than 1 mm can cause the material to exhibit a reduced visibility in the MR imaging because the spins dephase more rapidly, i.e. shorter T2* relaxation times are achieved. For example, the spatial resolution (i.e. the voxel size) of typical MR installations can in fact also have a magnitude of approximately 1 mm. This means that when capturing MR signals, averaging or integration takes place over a corresponding imaging volume of e.g. 1 mm³. If the susceptibility and hence the local magnetic field varies within this volume, a rate at which the nuclear spins contributing to the signal dephase can differ locally. When using a gradient echo sequence, for example, this can result in different echo time points. The signal intensity can decrease. This can reduce the MR visibility.

For example, the material can then have a T2* relaxation time of nuclear spins in the volume, which is less by a factor of 2 and preferably by a factor of 4 than the corresponding T2* relaxation time of the support material.

Material here denotes the material which comprises the support material and the doping material. The T2* relaxation time is known to a person skilled in the art with reference to magnetic field inhomogeneities, and relates to the transversal dephasing of the nuclear spins relative to the position of rest (spin-spin relaxation). The T2* relaxation time can denote e.g. the time, following a single 90° HF pulse, after which the transversal magnetization has returned to 37% of its initial value. The T2* time can be important for the signal strength or signal-noise ratio (so-called T2* weighted imaging) in the case of gradient echo MR recording sequences, for example.

The doping material exhibits an anisotropic susceptibility. This means that different degrees of susceptibility may be present along different directions, these being specified in relation to the crystal structure of the doping material, for example. In particular, there may be a preferred direction along which the value of the susceptibility of the doping material is highest. For example, a selective orientation along this preferred direction or relative to this preferred direction can result in the particularly large susceptibility variations being present locally, thereby achieving a significantly reduced T2* relaxation time and hence a particularly low visibility in the MR imaging of the material.

An extremely wide variety of materials are known to exhibit such anisotropy, e.g. graphite, graphene (multi-layer and single-layer), or carbon nanotubes. Graphite has a hexagonal layer structure. Orientation of the magnetization perpendicular to the graphite layers results in high demagnetization fields. Therefore e.g. the direction perpendicular to the graphite layers can exhibit particularly high susceptibility. It is e.g. possible to effect a mean orientation of the graphite layers as a doping material, such that the graphite layers are on average perpendicular to the predetermined direction.

The overall susceptibility for arbitrarily oriented magnetic moments is generally derived as follows:

$$3\chi_{tot} = \chi_x + \chi_y + \chi_z. \quad (A.1)$$

For graphite:

$$\chi_{tot} = \frac{1}{3} \cdot (\chi_s + 2\chi_p) = \frac{1}{3} \cdot (-595 \cdot 10^{-6} - 2 \cdot 8 \cdot 10^{-6}) = -204 \cdot 10^{-6} \quad (A.2)$$

where $\chi_s$ denotes the susceptibility perpendicular to the crystal plane and $\chi_s$ denotes the susceptibility parallel with the crystal plane.

By setting an average orientation, the following can be achieved:

$$(\chi_{tot} \approx \chi_s, \quad (A.3)$$

The orientation of the particles of the doping material can therefore be used as an additional parameter for checking the local or microscopic susceptibility and hence the magnetic field inhomogeneity.

A relationship can generally exist between the crystal structure of the doping material and the magnetic anisotropy. For example, particularly those doping materials having high aspect ratios can exhibit high levels of anisotropy in respect of their susceptibility. Corresponding conformities are known to a person skilled in the art, and therefore a detailed explanation is not required here. An alignment of the doping material in relation to the anisotropic susceptibility can be effected e.g. by melting down the support material, adding the doping material and simultaneously applying a magnetic field of specified strength and orientation. In this context, e.g. the orientation of the magnetic field can define the predetermined direction.

A mean orientation can signify that the orientation of individual grains or clusters of the doping material varies from the predetermined direction. For example, the material can exhibit a distribution of the orientation of the doping material, which distribution can be described by e.g. a Gaussian curve. However, the orientation averaged over a sufficiently large volume (e.g. 1 mm³) can be parallel with the predetermined direction. A measure for variability of the orientation of individual grains or clusters of the doping material can be a standard deviation of the orientation.

For example, the doping material can exhibit the mean orientation within the volume. As explained above in relation to the concentrations of the support material and doping material, local deviations in concentration and orientation from the macroscopic mean value can occur as a result of the intermixing. The macroscopic mean value for the volume can also be achieved in relation to the orientation of the doping material.

The mean orientation and/or a standard deviation of the mean orientation can also be location-dependent, said location dependency having a characteristic length of less than 1 mm. Specifically concerning this, a location dependency of the susceptibility (in addition to any influence due to local and microscopic concentration variations of the doping material) can also be achieved by a location dependency of the susceptibility value parallel with the basic magnetic field in the MR installation. Therefore an increase (decrease) in the standard deviation of the orientation can also cause a greater (lesser) effective local susceptibility.

For example, a location dependency of the mean orientation or of the standard deviation of the orientation can be achieved by a location dependency of the orientation or of the strength of the magnetic field that is used during the manufacture of the material.

For example, the mean orientation may result in a maximized susceptibility along the predetermined direction. In particular, an orientation of the doping material may actually be desired which aligns the direction of greatest susceptibility parallel with the predetermined direction. At the same time, this may allow the proportion of the doping material to be reduced in comparison with a case in which random orientation is present. This can result in cost savings. At the same time, e.g. electrical and mechanical material properties of the material may be advantageous.

The basic magnetic field can then be applied in the predetermined direction or at a specific angle relative to the predetermined direction in an MR installation. It is thus possible to achieve a particularly high level of location dependency in respect of the susceptibility and the local magnetic field, such that a particularly reduced T2* relaxation time is achieved.

A standard deviation of the mean orientation can also be less than 45°, preferably less than 20°, and most preferably less than 10°. The standard deviation of the mean orientation can be interpreted here as a measure for the quality of the orientation. For example, the variability of the orientation of individual grains or clusters of the doping material relative the predetermined direction can be dependent on a strength of the magnetic field that was used during the manufacture of the material and/or on a viscosity of the support material. It may be desirable to select the viscosity accordingly.

Concerning this, the local variation of the susceptibility or the visibility in the MR imaging caused by the admixed doping material can depend characteristically on the grain size of the doping material and the shape of the doping grains, for example. A grain size of the doping material can be smaller than 200 µm, preferably smaller than 10 µm. In particular, a grain size can be in the region of approximately 100 µm, for example. The term grain size can signify e.g. a mean grain size. The doping material can exhibit a distribution of the grain sizes in particular, which distribution can be described by e.g. a Gaussian curve. Corresponding scenarios are known to the person skilled in that art. Small grain sizes can also have advantages e.g. in respect of further properties of the material, e.g. robustness, conductivity, brittleness, etc.

For example, the proportion can lie in the range of 0.1%-80%, preferably in the range of 1%-20%, and most preferably in the range of 9%-11%. The percentages can signify percentages by weight or percentages by volume, for example.

In particular, the proportion can correlate directly to the macroscopic magnetic susceptibility of the material, i.e. the susceptibility that is measured as an average for a large piece of the material. Therefore e.g. a larger proportion of the doping material can result in the macroscopic magnetic susceptibility of the material having a larger absolute value. It may therefore be desirable on one hand to admix a large proportion of doping material to the support material. On the other hand, it may be desirable to preserve specific (e.g. electrical and mechanical) material properties of the material, which properties would be degraded by an excessive proportion of admixed doping material. For example, it may be desirable to obtain a particularly resistant material, which however becomes brittle as a result of admixing excessive proportions of the doping material.

Concerning this, the support material can be e.g. acrylonitrile butadiene styrole (ABS) plastic, for example. Such plastics are also known as Terluran plastics. In a particularly preferred embodiment, the support material can be e.g. ABS GP22.

The support material can generally be selected from the group comprising the following elements: thermoplastics, thermoplastic elastomers, elastomers, duroplastics, foams. Such materials exhibit preferred properties in terms of strength, elasticity, heat resistance, low electrical conductivity, magnetic properties etc. A Lexan plastic can also be used as support material.

Correspondingly, the doping material can be e.g. either diamagnetic (magnetic susceptibility <0) or paramagnetic (magnetic susceptibility >0). For example, the doping material can be selected from a first group of diamagnetic materials comprising the elements: graphite, carbon nanotubes, bismuth. However, it is also possible for the doping material to be selected from a second group of paramagnetic materials comprising the elements: platinum, chromium, tungsten, ferritin. It is also possible to use e.g. ferromagnetic nanoparticles having grain sizes smaller than 100 nm or smaller than 50 nm or smaller than 20 nm as a doping material. It is also possible to use palladium as a doping material. In particular, such materials can be used in conjunction with a comparatively large absolute value of the magnetic susceptibility, such that a local deviation of the magnetic field from the value of the basic magnetic field in the magnetic resonance installation becomes particularly large. This means that the local dephasing of the nuclear spins can differ significantly, resulting in a particularly low value for the T2* relaxation time.

For example, the material can exhibit a macroscopic magnetic susceptibility which is essentially equal to a susceptibility of water or tissue or organic material or air. Macroscopic susceptibility here can refer to, for example, that value of the susceptibility which is measured in the extreme case of large pieces of the material, i.e. with macroscopic dimensions. For such a piece, an average intermixture of the support material and the doping material or plurality of doping materials having different magnetic properties (diamagnetic/paramagnetic/ferromagnetic) may be present. The piece can have dimensions which are equal to or greater than the volume, for example. Values for the susceptibility of the above cited variables are known to the person skilled in the art and can be e.g. $\chi=9\cdot10^{-6}$ for water or tissue or $\chi=6\cdot10^{-6}$ for organic material or $\chi=0.38\cdot10^{-6}$ for air.

As explained above, the material according to that aspect of the invention presently under discussion can have the effect that the susceptibility varies locally due to a fine intermixture of the support material with the doping material. This can produce a particularly short T2* relaxation time and cause the material to exhibit reduced visibility in the MR imaging. If the material moreover still exhibits a macroscopic average susceptibility having one of the values cited above, this effect of the reduced MR visibility is accompanied by the further effect of susceptibility matching: e.g. susceptibility gradients can occur at the air-tissue interface, i.e. changes in the susceptibility can occur as a function of the location. For example, the value of the magnetic susceptibility changes from $\chi=0.38\cdot10^{-6}$ to $\chi=9\cdot10^{-6}$ at the skin surface. This can cause the local magnetic field value in and around this region to vary from the value of the basic magnetic field in the MR installation. MR imaging can then include so-called susceptibility artifacts in this region, e.g. displacements in the MR images, etc.

However, if the material has a correspondingly matched value, it is possible to ensure that no significant susceptibility gradients occur at the material-tissue interface if the material is used for MR installation components such as HF coils or shim cushions that are situated next to the body, for example. In other words, the susceptibility mismatch can be shifted to regions that do not contribute to the MR imaging. The susceptibility artifacts in the MR images can therefore be reduced.

However, it is also possible for the material to have a susceptibility that differs from the above cited values for water or tissue or organic material or air. This can be advantageous, for example, in order to achieve a particularly reduced MR visibility. In other words, the material properties can then be optimized in respect of reducing the MR visibility, this relating primarily to the microscopic location dependency of the susceptibility. The macroscopic susceptibility can be of secondary importance in this case.

In particular, it is e.g. possible for the material to comprise a further magnetic doping material which is admixed in a further proportion, wherein e.g. a homogeneous intermixture of the support material and the doping material and the further doping material may be present within the volume, and wherein an operational sign of a susceptibility of the further doping material can differ from an operational sign of a susceptibility of the doping material. Therefore the doping material can be paramagnetic and the further doping material can be diamagnetic (or vice versa), for example. It is also possible for the doping material or the further doping material to be ferromagnetic.

In such a case, it is possible to achieve the effect of a particularly short T2* relaxation time, for example, as the microscopic susceptibility gradients have particularly high values or many different local magnetic field strengths are present within a voxel of the MR imaging. At the same time, it is possible to adjust the value of the macroscopic susceptibility of the material in a suitable manner by means of specifically selecting the proportion and the further proportion as a function of the susceptibilities of the doping materials.

It is possible in general to admix N doping materials having a respective susceptibility $\chi_n$ to the support material (susceptibility $\chi_B$). The macroscopic susceptibility is then derived as follows:

$$\chi_m = \chi_B V_B + \sum_{i=1}^{N} V_{Dn}\chi_n \qquad (1)$$

where $V_B$, $V_{Dn}$ are the respective volume proportions of the support material and the doping materials respectively. It therefore applies that:

$$V_B + \sum_{i=1}^{N} V_{Dn} = 1. \qquad (2)$$

For example, applying equation 1 to two doping materials, namely graphite powder $\chi_{D1}=-205\cdot10^{-6}$ and palladium powder $\chi_{D2}=-806\cdot10^{-6}$ these being admixed by $V_{D1}=5.20\%$ and $V_{D2}=0.20\%$ respectively to a non-magnetic $\chi_B=0$ support material, it follows that: $\chi_m=-9\cdot10^{-6}$. This corresponds to a value of human tissue. The support material can be e.g. ABS GP22 in this context.

It would also be possible to admix $V_{D1}=5\%$ graphite and $V_{D2}=0.50\%$ or $V_{D2}=1.00\%$ palladium to this support material, giving macroscopic susceptibilities of −6.6 ppm and −2.6 ppm respectively.

The above examples are purely illustrative. The proportion and the further proportion can generally be different, such that a macroscopic susceptibility equals a specific value. In particular, the macroscopic susceptibility of the material can equal e.g. the value of water, air, tissue or organic material as a result of admixing a doping material and a further doping material. In particular, the grain size of the further doping material can also be smaller than e.g. 200 µm, preferably smaller than 100 µm, and most preferably smaller than 10 µm. Corresponding or identical requirements to those described above in relation to the doping material can generally be applied to the further doping material.

In particular, it is possible in this context for the further doping material to exhibit an anisotropic susceptibility. In respect of its anisotropic susceptibility, the further doping material can exhibit a mean orientation along the predetermined direction. In such a case, it is possible to achieve effects for the further doping material which correspond to those effects that can be achieved for the doping material as described above.

It is also possible for a standard deviation of the orientation of the doping material and a standard deviation of the mean orientation of the further doping material to differ. This can be caused e.g. by different crystal structures, which allow the doping materials to be aligned more readily or less readily with the support material for a given viscosity. In particular, it is thereby possible selectively to influence the microscopic location dependency of the susceptibility and the macroscopic susceptibility of the material.

According to a further aspect, the invention relates to a method for manufacturing a material for use in a magnetic resonance installation. The method comprises the fusing of a support material (made of plastic) by means of an extruder and the admixing of a proportion of a magnetic doping material, wherein the doping material exhibits an anisotropic susceptibility and the admixture is effected such that a homogeneous intermixture of the support material with the doping material is present within a volume of less than 1 mm³. The method further comprises the application of a magnetic field to the mixed material along a predetermined direction, such that the doping material exhibits a mean orientation along the predetermined direction in respect of its anisotropic susceptibility.

Since the magnetic anisotropy of the susceptibility can also correlate to the crystal structure of the doping material, the shape of the doping material can also be used for the alignment. For this purpose, e.g. flow effects during the manufacture of a plastic injection-molded part from the material having the shape of the doping material can be used to achieve an orientation of the direction of e.g. maximal susceptibility along the predetermined direction. In this way, it is possible to maximize the shape-dependent demagnetization factors at the same time.

For example, the magnetic field can be applied with a location dependency in respect of its strength and/or its orientation, such that the mean orientation and/or the standard deviation of the orientation exhibits the location dependency, said location dependency having a characteristic length of less than 1 mm.

A location dependency of the susceptibility on microscopic length scales can be achieved e.g. by means of the local concentration variations of the doping material as explained above. However, it is also possible to achieve a location dependency of the susceptibility by means of a location dependency of the orientation or the standard deviation of the orientation of the doping material in respect of its anisotropic susceptibility. This can have the advantage that the location dependency is particularly easy to control. It is typically possible in fact to control the strength and orientation of the magnetic field with particular precision during the manufacture. However, deterministic microscopic control of the intermixture of the support material and the doping material may not be possible, and said intermixture may be subject to statistical conformities.

Using a material which is manufactured in accordance with the method presently under discussion, it is possible to achieve effects that correspond to those effects that can be achieved using a material for use in an MR installation according to a further aspect of the invention.

According to a further aspect, the invention relates to a magnetic resonance installation which has a sensitive region, wherein said magnetic resonance installation is so configured as to capture magnetic resonance data within the sensitive region for the purpose of imaging, wherein said magnetic resonance installation comprises components within the sensitive region for the purpose of imaging. The magnetic resonance installation is characterized in that the components comprise a material for use in a magnetic resonance installation according to a previously discussed aspect of the invention. For example, the components can relate to high-frequency coils, a table or a couch for introducing the patient into the MR installation or shim cushions. If a material according to an aspect of the invention is used for the manufacture of such components, these components can exhibit a reduced visibility in the MR imaging. It is advantageous that these components can also have a magnetic susceptibility that is matched to the susceptibility of the environment, such that susceptibility artifacts can be reduced in the MR imaging.

In particular, the components can be so arranged that the predetermined direction is essentially parallel with a fundamental effect of the MR installation. This means that e.g. a particularly large component of the susceptibility of the doping material can then be parallel with the basic magnetic field. A particularly low visibility of the material in the MR images can be achieved thereby.

The features of the above described embodiment variants and aspects of the invention can obviously be combined with each other. In particular, the features can be used not only in the described combinations but also in other combinations or individually without thereby departing from the scope of the invention.

BRIEF DESCRIPTION OF THE DRAWINGS

The above described properties, features and advantages of this invention and the way in which these are achieved become clearer and more readily understandable in connection with the following description of the exemplary embodiments, which are explained in greater detail with reference to the drawings, wherein.

DETAILED DESCRIPTION OF INVENTION

Figure 1:
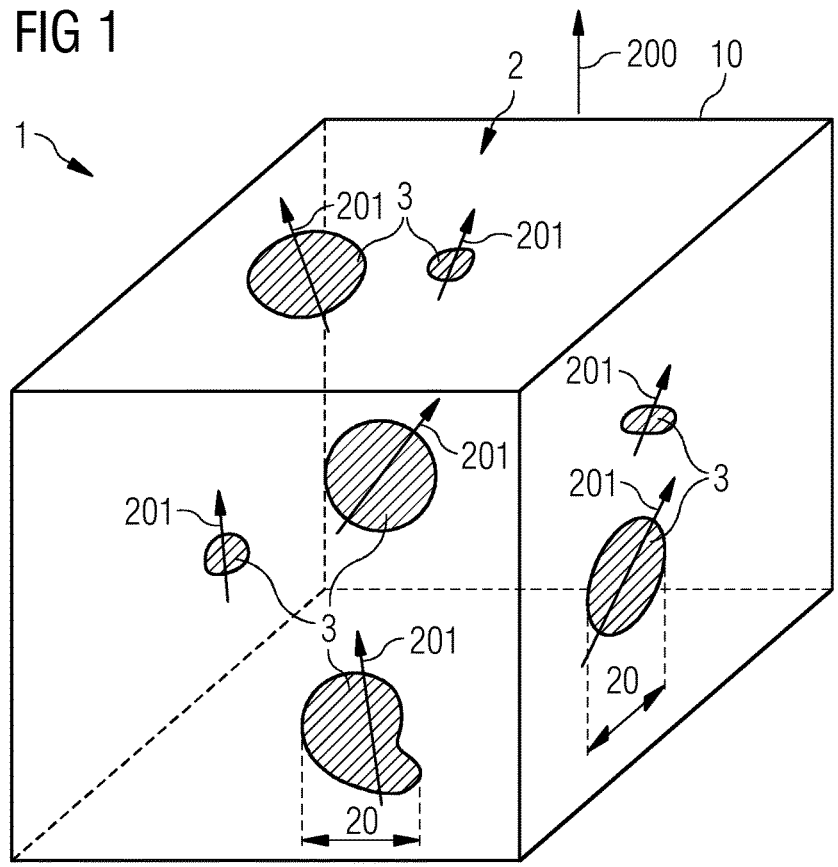
FIG. 1 shows a material comprising a support material and an admixed doping material whose susceptibility is aligned along a predetermined direction.

The present invention is explained in greater detail below on the basis of preferred embodiment variants and with reference to the drawings. Identical reference characters in the figures designate identical or similar elements.

FIG. 1 shows a material 1 which is composed of a support material 2 and an admixed doping material 3. The doping material is shown as grains or clusters that are embedded in the support material 2. A grain size 20 is indicated.

Figure 2:
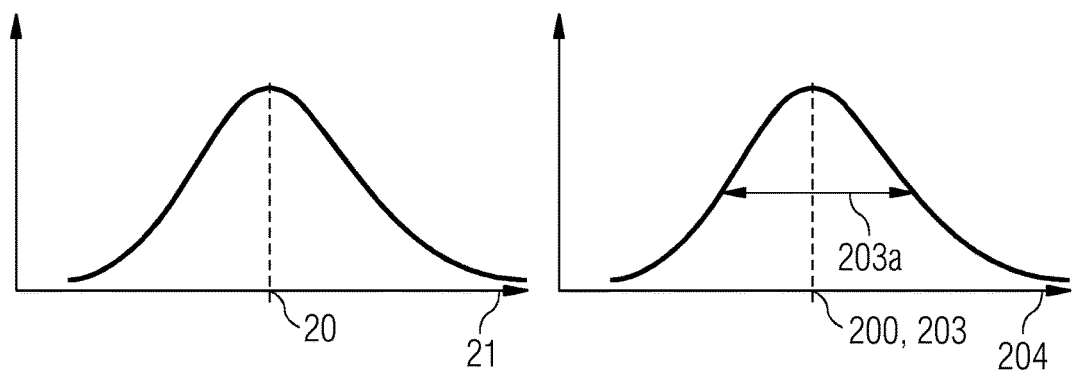
FIG. 2 shows a grain size distribution of the doping material and a distribution of the orientation of the susceptibility.

A grain size distribution 21 (i.e. a frequency of different grain sizes) is shown by way of example on the left-hand side of FIG. 2. The maximum of the grain size distribution 21 can refer to the grain size 20, for example. The grain size distribution 21 is described by a Gaussian curve in FIG. 2. For example, the grain size 20 can be smaller than 200 µm, preferably smaller than 100 µm, and most preferably smaller than 10 µm.

Referring again to FIG. 1, local deviations in concentration of the doping material or of the support material from a macroscopic mean value of the concentrations are clearly present. This is due to the grains or clusters of the doping material 3. A homogeneous intermixture, i.e. an intermixture in which the concentrations of support material and doping material correspond to the macroscopic value in the extreme case of large volumes, is achieved in a volume 10 having a size of 1 mm$^3$. In other words, the concentration of the relevant materials 2, 3 varies microscopically with a characteristic length of approximately 1 mm. If larger lengths are used for averaging, values equal to the macroscopic mean value are obtained.

Such parameters depend e.g. on the production process. For example, a pretreatment of the doping material can result in a smaller grain size and hence a particularly homogeneous and fine intermixture. The support material 2 can be a plastic such as ABS GP22, for example. The use of e.g. a twin screw extruder for melting down the plastic can provide a particularly fine and homogeneous intermixture.

The doping material 3 is a magnetic material, i.e. it has a magnetic susceptibility which is not equal to 0. The doping material 3 can be e.g. ferromagnetic, diamagnetic or paramagnetic. In particular, the doping material 3 can exhibit a magnetic susceptibility which differs from the magnetic susceptibility of the support material 2. This results in the occurrence of susceptibility changes, i.e. local variations in the susceptibility on the characteristic length scale cited above, i.e. within the volume 10. This means that different susceptibility values are present depending on the location within the volume 10. The doping material 3 can be graphite or carbon nanotubes or bismuth or platinum or chromium or tungsten or ferritin or palladium, for example. It can be admixed in proportions of e.g. 5-15 percent by weight or percent by volume.

The material 1 can be used for components within an MR installation, for example. A basic magnetic field for polarizing the nuclear spins is typically present there. As a result of the locally differing susceptibilities within the volume 10, the basic magnetic field 10 varies within the volume 10. Therefore nuclear spins at different locations within the volume 10 dephase at different speeds. If the MR installation integrates over the volume 10 for the purpose of MR imaging, the material 1 exhibits reduced visibility because the T2* relaxation time is reduced. In particular, this can apply to so-called gradient echo MR recording sequences, these being known to the person skilled in the art. Integration over the volume 10 (so-called voxels) for the purpose of MR imaging may be required e.g. due to a limited spatial resolution of the MR installation or due to limited sensitivity, making it necessary to capture correspondingly accumulated measured values in order to increase a signal-to-noise ratio.

It should be understood that a comparatively smaller reduction of the T2* relaxation time may be present in the case of a less homogeneous intermixture of the material 1, e.g. in particular an intermixture of the material on a characteristic length scale that is larger than the spatial resolution of the MR installation. This specifically means that less variation of the magnetic field strength may then occur within the volume 10, such that different dephasing conditions for the nuclear spins are not present.

Figure 7:
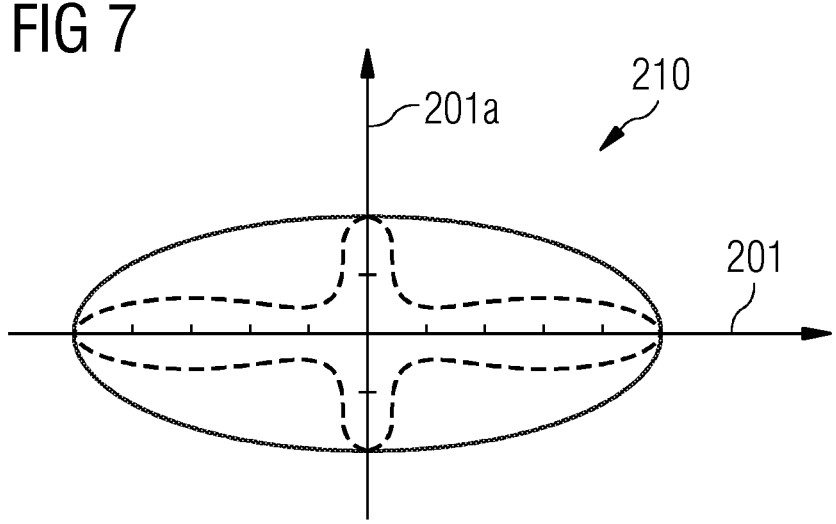
FIG. 7 is a polar plot of a susceptibility of the doping material and illustrates a magnetic anisotropy.
Figure 8:
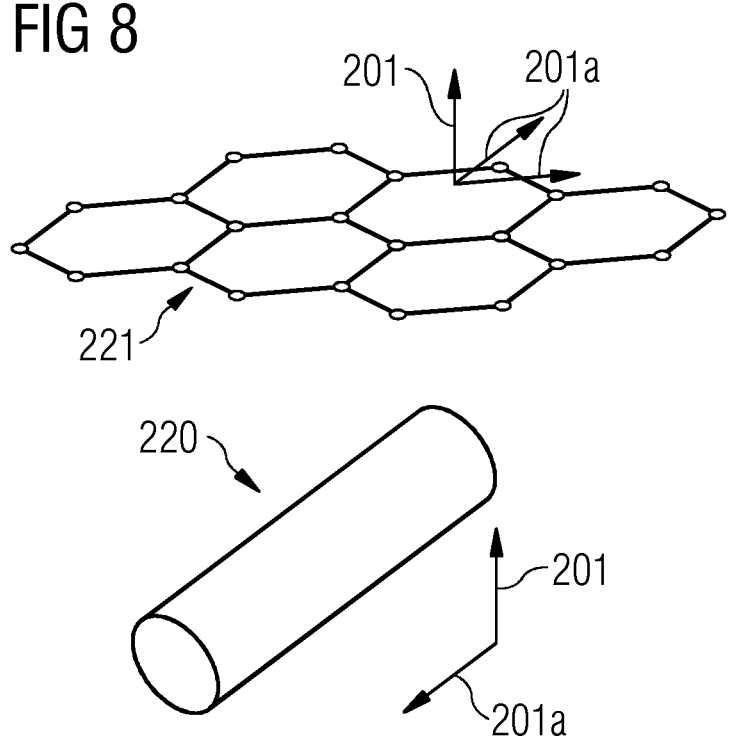
FIG. 8 illustrates the magnetic anisotropy of graphite and carbon nanotubes.

The doping material 3 in FIG. 1 exhibits an anisotropic susceptibility. This means that there exists a direction 201 of maximal absolute susceptibility or so-called hard axis. FIG. 7 illustrates the magnetic anisotropy by means of a polar plot of the susceptibility (continuous and broken lines). An absolute value of the anisotropy is shown. It is evident here that directions 201*a* of lesser susceptibility may also exist. The orientation of the hard axis 201 may be determined e.g. by a crystal structure of the doping material 3. The upper part of FIG. 8 illustrates the alignment of the hard axis 201 for diamagnetic graphite 221 disposed in a hexagonal layer structure. The hard axis 201 runs perpendicular relative to the layer plane. The lower part of FIG. 8 illustrates the corresponding situation for carbon nanotubes 220. The hard axis 201 runs perpendicular relative to the longitudinal axis of the tubes 220.

As shown in FIG. 1, the doping material 3 is so oriented that the axis of maximal absolute susceptibility 201 is parallel with the predetermined direction 200 over the volume 10. However, individual grains or clusters of the doping material 3 may have an orientation that deviates from the direction 200. This is shown on the right-hand side of FIG. 2, where a distribution of the orientation 204 is shown. The distribution of the orientation 204 is described by a Gaussian distribution with specific standard deviation of the orientation 203*a*. The maximum of the distribution 204, i.e. the mean orientation 203, is parallel with the predetermined direction 200.

This can have the effect that, assuming a corresponding alignment of the basic magnetic field parallel with the direction 200, a maximal location dependency of the susceptibility on the characteristic length scale can be achieved in the MR installation. It is thereby possible to achieve a particularly reduced visibility of the material 1 in the MR imaging.

Figure 3:
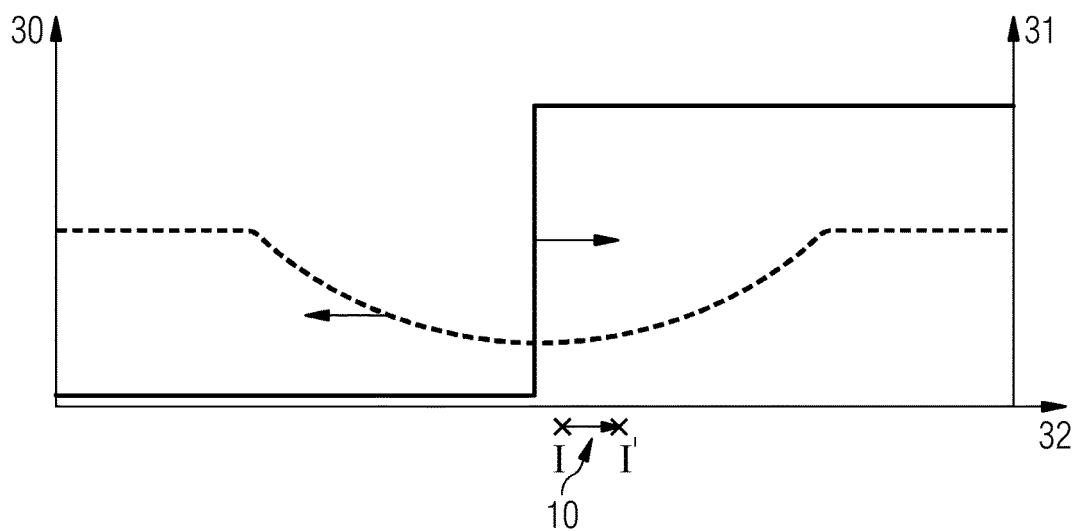
FIG. 3 shows a magnetic field variation on a first characteristic length scale due to a susceptibility mismatch.
Figure 4:
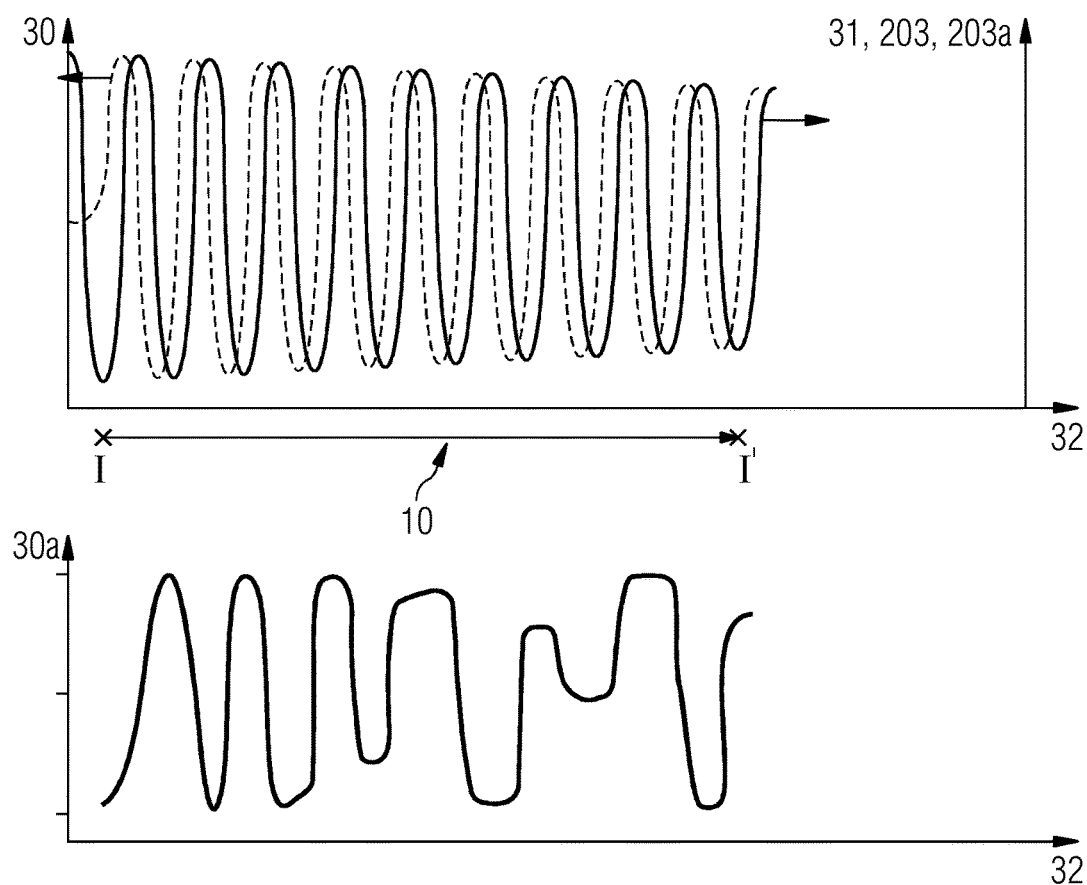
FIG. 4 shows a magnetic field variation on a second characteristic length scale due to microscopic susceptibility gradients and the orientation of the susceptibility, wherein the second characteristic length scale is smaller than the characteristic length scale in FIG. 3.

The various cited characteristic length scales are shown in FIGS. 3 and 4. In FIG. 3, for an abrupt jump in the local susceptibility 31 (continuous line, right-hand scale), a value of the magnetic field 30 (broken line, left-hand scale) is shown as a function of the location 32. It can be seen from FIG. 3 that the value of the magnetic field 30 deviates from a constant value (e.g. the value of the basic magnetic field in the MR installation) in a region around the susceptibility jump. The jump can occur at a transition point from air to human tissue, i.e. at the skin surface, for example.

A typical length scale in FIG. 3, i.e. a length scale on which the value of the magnetic field 30 varies, is represented by centimeters, e.g. 5-10 cm. A voxel or a spatial resolution of a typical MR installation is considerably smaller, however, and a spatial resolution of 1 mm is achieved in typical MR installations. A side length of the corresponding volume 10 is indicated for the length I-I'. However, there is little or no variation in the magnetic field 30 on such a length scale in the scenario according to FIG. 3. An essentially homogeneous magnetic field would therefore be present within a voxel, and little or no reduced MR visibility would be achieved.

In the upper part of FIG. 4, the value of the magnetic field 30 is correspondingly shown as a function of the location 32 for a susceptibility 31 which varies on a considerably shorter length scale. Like the susceptibility 31, the orientation of the doping material 3 or the standard deviation of the orientation 203*a* can also vary. This again results in a corresponding location dependency of the susceptibility 31. Identical lengths I-I' are indicated in both FIG. 3 and FIG. 4. Such a variation in the susceptibility 31 as a function of the location 32 can be achieved, e.g. for the material 1 according to one aspect of the invention, if the intermixture of support material and doping material 2,3 within the volume 10 of less than 1 mm³ is homogeneous, i.e. a particularly fine intermixture is present. The length I-I' can designate a length of 1 mm, for example. As shown in FIG. 4, the magnetic field 30 within a voxel of the MR imaging can then have different values, such that the T2* relaxation time of the material 1 is reduced, e.g. by a factor of 2 or 4 relative to the T2* relaxation time of the support material 2.

The lower part of FIG. 4 shows an orientation 30*a* of the magnetic field. Since the magnetization of the grains of the doping material 3 (see FIG. 1) can be oriented differently in general, the orientation 30*a* of the magnetic field can also vary on the characteristic length scale. This can also have an influence on the T2* relaxation time.

Figure 5:
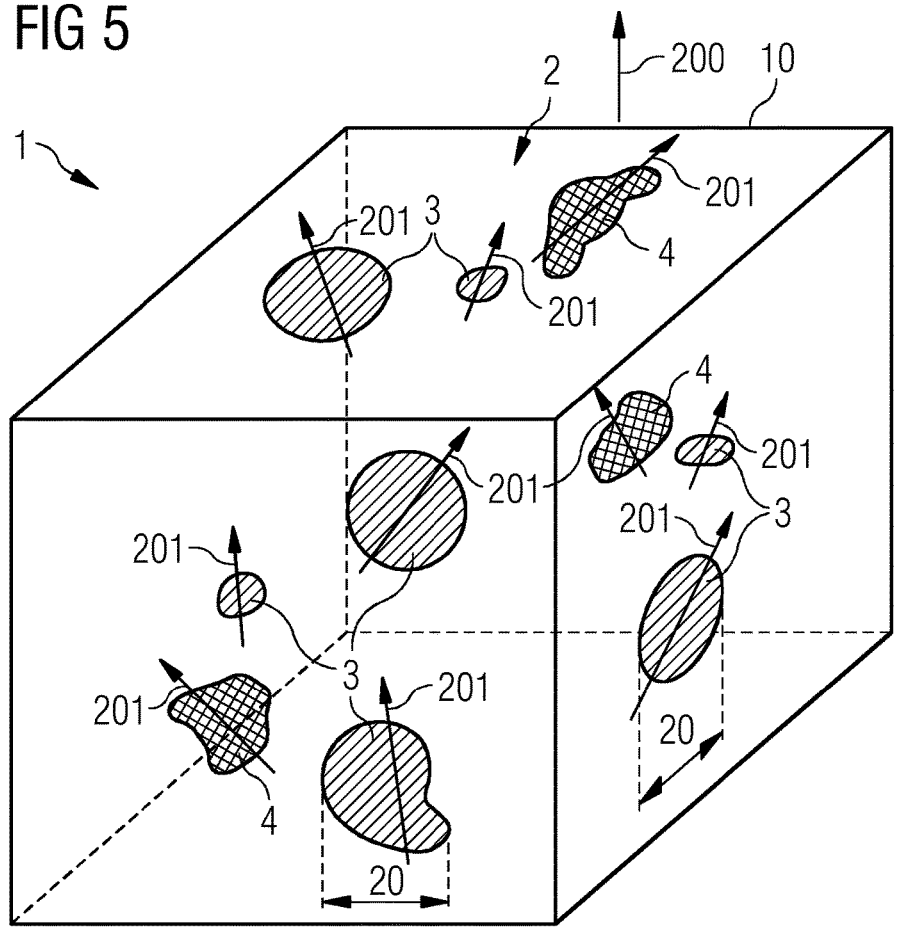
FIG. 5 shows a material comprising a support material and an admixed doping material and a further doping material.

FIG. 5 shows the material 1 which, in addition to the doping material 3, comprises a further doping material 4. The further doping material 4 can also be magnetic. In particular, the further doping material 4 can exhibit a magnetic susceptibility which has a different operational sign to that of the magnetic susceptibility of the doping material 3. In other words, the doping material 3 can be paramagnetic or ferromagnetic (diamagnetic) while the further doping material 4 is diamagnetic (paramagnetic or ferromagnetic), for example.

Two effects can be achieved as a result of using the material 1. Firstly, the location dependency of the susceptibility within the volume 10 can be particularly marked. The local magnetic field can therefore vary significantly, such that the T2* relaxation time of the nuclear spins can be reduced significantly. The material 1 can therefore exhibit reduced visibility in the MR imaging. Secondly, by means of selecting suitable proportions of the doping materials 3, 4 on the basis of their susceptibilities, it is possible to ensure that the macroscopic susceptibility of the material 1 is equal to a predetermined value, e.g. equal to air, water, tissue or organic material. This is described by equations 1 and 2 above. This can allow the susceptibility artifacts in the MR imaging to be reduced. Susceptibility artifacts can occur due to local deviations in the magnetic field strength 30, as illustrated in FIG. 3. However, it should be understood that the relevant length scales for these two effects have different magnitudes, as explained above with reference to FIGS. 3 and 4.

The doping materials 3, 4 in FIG. 5 are characterized by a magnetic anisotropy. The hard axis 201 of the doping materials 3, 4 is parallel with the predetermined direction 200 on average. In general, a standard deviation of the orientation of the doping materials 3,4 can assume different values due to e.g. different grain sizes, etc.

Figure 6:
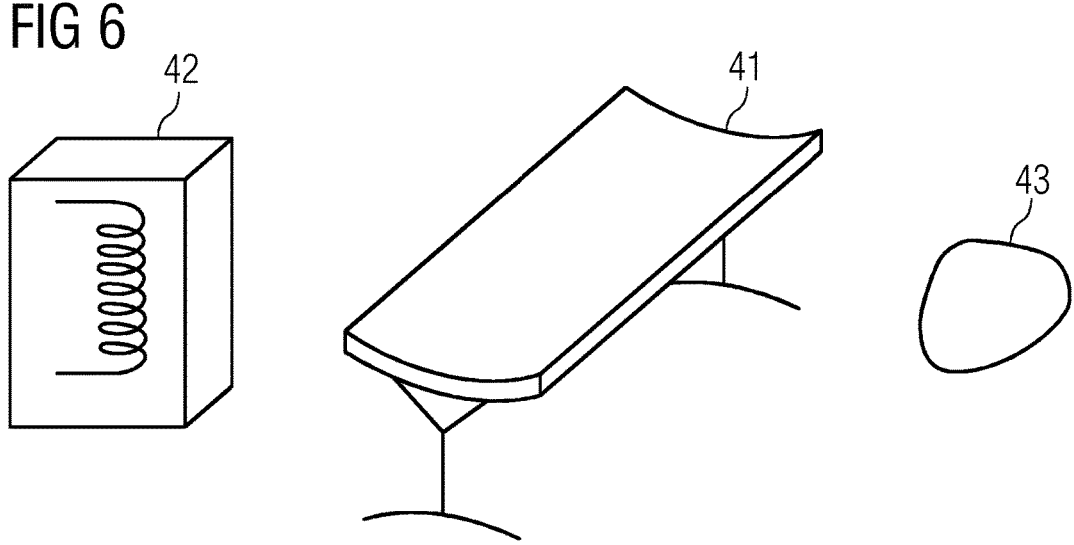
FIG. 6 illustrates components of an MR installation.

FIG. 6 illustrates exemplary components 41, 42, 43 which can be made partly or predominantly from the material 1. A table or couch 41 is shown on which a patient can be introduced into the MR installation. Also shown is a HF local coil 42, which can be used to capture MR signals or to excite the magnetization by means of irradiation using HF pulses. A shim cushion 43 is also shown. The shim cushion 43 exhibits a specific susceptibility, e.g. the susceptibility of human tissue. If the shim cushion is placed next to the human body during the MR imaging, a jump in the susceptibility as illustrated in FIG. 3 occurs at locations which are not part of the MR imaging (e.g. at the interface between air and shim cushion). In this way, it is possible to reduce susceptibility artifacts next to the skin, for example.

It is therefore possible to achieve a reduction in the MR visibility of the material 1 by means of doping the MR imaging support material 2 using magnetic or weak magnetic doping materials 3, 4, these being embodied as e.g. microparticles or nanoparticles. This means in particular that all common materials, e.g. conventional plastics, can also be utilized in imaging volumes of the MR installation. Therefore costs can be saved, new mechanical functions can be realized, e.g. more flexible coils, coils with plastic joints, lighter patient tables, etc., and the comfort of the patient can be improved. In particular, thermoplastics, thermoplastic elastomers, elastomers, duroplastics and foams are suitable as support materials 2. Diamagnetic materials (in particular strongly diamagnetic materials such as graphite and bismuth) and the whole range of paramagnetic materials are suitable as doping materials 3. The doping material 3 or the further doping material 4 can be added in a range of 1-80 percent by weight, preferably in a range of 5-15 percent by weight, most preferably in a range of 9-11 percent by weight. The particle size can be e.g. 100 µm, preferably smaller than 10 µm. In particular, ferromagnetic materials can also be utilized in the case of nanoparticles having grain sizes of less than 100 nm.

Use of twin screw extruders is advantageous when preparing the mixture of the support material 2 and the doping materials 3, 4, as a particularly fine and homogeneous distribution and thorough mixing of the materials 2, 3, 4 is achieved thus.

While specific embodiments have been described in detail, those with ordinary skill in the art will appreciate that various modifications and alternative to those details could be developed in light of the overall teachings of the disclosure. For example, elements described in association with different embodiments may be combined. Accordingly, the particular arrangements disclosed are meant to be illustrative only and should not be construed as limiting the scope of the claims or disclosure, which are to be given the full breadth of the appended claims, and any and all equivalents thereof. It should be noted that the term "comprising" does not exclude other elements or steps and the use of articles "a" or "an" does not exclude a plurality.

The invention claimed is:

1. A material for use in a magnetic resonance installation, the material comprising:
   a support material; and
   a magnetic doping material which is admixed in a specific proportion with the support material for manufacturing the material for use in the magnetic resonance installation,
   wherein the doping material exhibits an anisotropic susceptibility,
   wherein the doping material exhibits a mean orientation along a predefined direction with respect to the anisotropic susceptibility, and
   wherein an essentially homogeneous intermixture of the support material and the doping material is present within a volume of the material which is smaller than 1 mm$^3$ corresponding to a magnetic resonance imaging volume of the magnetic resonance installation, and
   wherein the material exhibits a macroscopic magnetic susceptibility which is essentially equal to a susceptibility of water or tissue or organic material or air.

2. The material as claimed in claim 1, wherein the doping material exhibits the mean orientation within the volume of the material.

3. The material as claimed in claim 1, wherein the mean orientation and/or a standard deviation of the mean orientation exhibits a location dependency, and wherein the location dependency has a characteristic length of less than 1 mm.

4. The material as claimed in claim 1, wherein the mean orientation results in a maximized susceptibility along the predetermined direction.

5. The material as claimed in claim 1, wherein a standard deviation of the mean orientation is less than 45°.

6. The material as claimed in claim 1, wherein a grain size of the doping material is smaller than 200 µm.

7. The material as claimed in claim 1, wherein the specific proportion of the magnetic doping material admixed in the support material lies in the range of 0.1%-80%.

8. The material as claimed in claim 1, wherein the support material is selected from the group consisting of thermoplastics, thermoplastic elastomers, elastomers, duroplastics, foams, acrylonitrile butadiene styrole (ABS) plastic, and a combination thereof.

9. The material as claimed in claim 1, wherein the doping material is selected from
a first group of diamagnetic materials consisting of graphite, carbon nanotubes, bismuth, and a combination thereof; or
a second group of paramagnetic materials consisting of platinum, chromium, tungsten, ferritin, and a combination thereof.

10. The material as claimed in claim 1, wherein the material exhibits a macroscopic magnetic susceptibility which is not equal to at least a susceptibility of water and tissue and organic material and air.

11. The material as claimed in claim 1, wherein the material has a T2*-relaxation time of nuclear spins in the volume, which is less by a factor of 2 than the corresponding T2*-relaxation time of the support material.

12. The material as claimed in claim 1,
wherein the material comprises a further magnetic doping material which is admixed in a further proportion,
wherein an operational sign of a susceptibility of the further doping material differs from an operational sign of a susceptibility of the doping material, and
wherein an essentially homogeneous intermixture of the support material and the doping material and the further doping material is present within the volume.

13. The material as claimed in claim 12, wherein the further doping material exhibits an anisotropic susceptibility, and wherein the further doping material exhibits a mean orientation along the predetermined direction in respect of the anisotropic susceptibility.

14. The material as claimed in claim 13, wherein a standard deviation of the mean orientation of the doping material and a standard deviation of the mean orientation of the further doping material are different.

15. A method of manufacturing a material for use in a magnetic resonance installation, the method comprising:
fusing a support material, which is made of plastic, by an extruder,
admixing a proportion of a magnetic doping material with the support material for manufacturing the material for use in the magnetic resonance installation, wherein the doping material exhibits an anisotropic susceptibility, and wherein an admixture is effected such that a homogeneous intermixture of the support material with the doping material is present within a volume of less than 1 mm$^3$ corresponding to a magnetic resonance imaging volume of the magnetic resonance installation, and
applying a magnetic field to the mixed material along a predetermined direction, such that the doping material exhibits a mean orientation along the predetermined direction in respect of the anisotropic susceptibility.

16. The method as claimed in claim 15,
wherein the magnetic field is applied with a location dependency with respect to an orientation and/or strength such that the mean orientation and/or a standard deviation of the orientation exhibits the location dependency,
wherein the location dependency has a characteristic length of less than 1 mm.

17. A magnetic resonance installation having a sensitive region, wherein the magnetic resonance installation is configured as to capture magnetic resonance data within the sensitive region for the purpose of imaging, wherein the magnetic resonance installation comprising:
components within the sensitive region for the purpose of imaging,
wherein the components comprise a material comprising a support material and a magnetic doping material which is admixed in a proportion with the support material,
wherein the doping material exhibits an anisotropic susceptibility,
wherein the doping material exhibits a mean orientation along a predefined direction with respect to the anisotropic susceptibility,
wherein an essentially homogeneous intermixture of the support material and the doping material is present within a volume of the material which is smaller than 1 mm$^3$ corresponding to a magnetic resonance imaging volume of the magnetic resonance installation, and
wherein the material exhibits a macroscopic magnetic susceptibility which is essentially equal to a susceptibility of water or tissue or organic material or air.

18. The magnetic resonance installation as claimed in claim 17, wherein the components are arranged such that the predetermined direction is essentially parallel with a basic magnetic field of the magnetic resonance installation.

* * * * *